United States Patent
Lai

(10) Patent No.: US 8,039,783 B2
(45) Date of Patent: Oct. 18, 2011

(54) METHODS AND MATERIALS FOR DETECTING LIGHT RELEASED FROM A LABELING MATERIAL USING SELF TRIGGERING EXCITATION

(75) Inventor: Benny Wing Hung Lai, Fremont, CA (US)

(73) Assignee: Alverix, Inc., San Jose, CA (US)

( * ) Notice: Subject to any disclaimer, the term of this patent is extended or adjusted under 35 U.S.C. 154(b) by 487 days.

(21) Appl. No.: 12/353,577

(22) Filed: Jan. 14, 2009

(65) Prior Publication Data
US 2010/0176274 A1    Jul. 15, 2010

(51) Int. Cl.
*H01J 40/14* (2006.01)
*G01J 1/32* (2006.01)
(52) U.S. Cl. .................................... 250/214 R; 250/205
(58) Field of Classification Search .................. 250/576, 250/458.1, 205, 214 R, 459.1, 461.1–462.1; 356/39–42, 51
See application file for complete search history.

(56) References Cited

U.S. PATENT DOCUMENTS

| | | | | |
|---|---|---|---|---|
| 5,212,386 A | * | 5/1993 | Gratton et al. | 250/458.1 |
| 2006/0214091 A1 | * | 9/2006 | Richter et al. | 250/214 R |
| 2010/0285599 A1 | * | 11/2010 | Schliesser et al. | 436/94 |

* cited by examiner

*Primary Examiner* — Que T Le
*Assistant Examiner* — Pascal M Bui Pho
(74) *Attorney, Agent, or Firm* — K&L Gates LLP

(57) ABSTRACT

The present disclosure relates generally to methods and materials for detecting light released from a labeling material using self triggering excitation. In particular, the present disclosure provides an architecture for a detection system that detects accumulated phase shifts in the form of a ring-oscillator frequency. The present disclosure provides devices for detection of a light released by a labeling material, the device comprising: a start-up circuit that provides power to a pulse generator block that drives an LED driver, a photodetector that detects the light released by a labeling material and provides a first signal; a variable reference that provides a second signal; a slicer for comparing the first signal to the second signal, wherein the slicer generates an output signal with a delay that triggers the pulse generator block after the start-up circuit is disabled; a frequency reference; and a frequency counter for comparing the output from the slicer to the frequency reference thereby producing a output signal.

44 Claims, 2 Drawing Sheets

METHODS AND MATERIALS FOR DETECTING LIGHT RELEASED FROM A LABELING MATERIAL USING SELF TRIGGERING EXCITATION

BACKGROUND

Assay test kits currently are available for testing a wide variety of medical and environmental conditions or compounds, such as a hormone, a metabolite, a toxin, or a pathogen-derived antigen. Most commonly these tests are used for medical diagnostics either for home testing, point of care testing, or laboratory use. For example, lateral flow tests are a form of immunoassay in which the test sample flows along a solid substrate via capillary action. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

In the field of immunoassay detection, the presence of an antigen may be inferred by the presence of specially created antibodies which contain reflectance or fluorescence labeling materials. The fluorescence material may be excited with a light pulse, and the fluorescence decay may be detected soon after the excitation source has been turned off. The period during this after-glow yields the best signal-to-noise ratio of the immunoassay labels, since the excitation source is turned off, thereby eliminating any background signal. To further improve the sensitivity, a method of detection known as time resolved fluorescence detection may be employed (see, e.g., FIG. 1). Generally, the labeled material 25 may be illuminated with a pulsed light source, such as with a laser or LED 20. After the light source has been turned off, the amount of fluorescence after-glow may then be detected with a light detector, such as a PIN photodiode 30, and its signal amplified with a transimpedance amplifier (TIA) 40. With further signal amplification 50, the signal may be applied to a Sample/Hold Circuit 60, where the output is further averaged usually by filtering 70. The final output 75 may then be measured with an Analog-to-Digital Converter (ADC) 80, and further processed with a micro-controller 90 to deliver the signal to a user-friendly output, such as an LCD display 100.

SUMMARY

The present disclosure provides methods and materials for detecting a light released from a labeling material.

The present disclosure provides an architecture that may be employed by devices for detection of a light released by a labeling material, the device comprising: a start-up circuit that triggers a pulse generator block that drives an LED driver, a photodetector that detects the light released by a labeling material and provides a first signal; a variable reference that provides a second signal; a slicer for comparing the first signal to the second signal, wherein the slicer generates an output signal with a delay that triggers the pulse generator block to drive the LED driver after the start-up circuit is disabled; a frequency reference; and a frequency counter for comparing the frequency of the output pulses of the slicer to the frequency reference, thereby producing an output signal.

In an embodiment, the start-up circuit is a pulsed current source.

In an embodiment, the labeling material is a fluorescent material.

In an embodiment, the photodetector is a PIN photo diode.

In an embodiment, the reference frequency signal is from a crystal source.

In an embodiment, the device further comprises a transimpedance amplifier for amplifying the signal produced by the photodetector.

In an embodiment, the device further comprises a light source for excitation of the fluorescent label. In an embodiment, the light source is a laser. In an embodiment, the light source is a LED.

In an embodiment, the device further comprises a delay block to set a nominal period.

In an embodiment, the device further comprises displaying the output signal on an output device. In an embodiment, the output device is an LCD display.

The present disclosure also provides methods for detecting a light released by a labeling material, said method comprising: a startup circuit to trigger a pulse generator block; pulsing the labeling material with a light source, wherein the labeling material releases a light; detecting the light released from the labeling material to produce a first signal; comparing the first signal produced by the labeling material to a second signal generated by a variable reference with a slicer to produce an output signal, wherein the output signal has a frequency and triggers the pulse generator block to drive the LED driver after the start-up circuit is disabled; comparing frequency of the output pulses of the slicer to the frequency reference; and obtaining a measurement from the frequency converter.

In an embodiment, the device further comprises converting the measurement from the frequency converter to a digital output that can be displayed on a user friendly interface. In an embodiment, the user friendly interface is an LCD display.

In an embodiment, the light is amplified to a voltage signal by a transimpedance amplifier.

In an embodiment, the light source is an LED. In an embodiment, the light source is a laser.

In an embodiment, the variable reference is set above a background level.

In an embodiment, the light is pulsed.

In an embodiment, the first and second signal are compared by a slicer.

In an embodiment, the light is detected by PIN photo diode.

In an embodiment, the frequency reference is from a crystal source.

In an embodiment, the device further comprises a transimpedance amplifier for amplifying the signal produced by the photodetector.

In an embodiment, the device further comprises a delay block to set a nominal period.

In an embodiment, the labeling material is a fluorescent material.

The present disclosure also provides methods for conducting an assay, the methods comprising: applying a test sample with at least one analyte to the assay; binding a labeling material to the analyte; providing power to a startup circuit to trigger a pulse generator block; pulsing the labeling material with a light source, wherein the labeling material releases a light; detecting the light released from the labeling material to produce a first signal; comparing the first signal produced by the labeling material to a second signal generated by a variable reference with a slicer to produce an output signal, wherein the output signal has a frequency and triggers the pulse generator block to drive the LED driver after the start-up circuit is disabled; comparing frequency from the output of the slicer to the frequency reference; and obtaining a measurement from the frequency converter.

In an embodiment, the assay is a lateral flow assay.

In an embodiment the method further comprises converting the measurement from the frequency converter to a digital output that can be displayed on a user friendly interface.

In an embodiment, the user friendly interface is an LCD display.

In an embodiment, the light is amplified to a voltage signal by a transimpedance amplifier.

In an embodiment, the output is displayed with a LCD display. In an embodiment, the light source is an LED. In an embodiment, the light source is a laser.

In an embodiment, the variable reference is set above a background level.

In an embodiment, the light is pulsed.

In an embodiment, the first and second signal are compared by a slicer.

In an embodiment, the light is detected by PIN photo diode.

In an embodiment, the frequency reference is from a crystal source.

In an embodiment the method further comprises a transimpedance amplifier for amplifying the signal produced by the photodetector.

In an embodiment the method further comprises a delay block to set a nominal period.

In an embodiment, the labeling material is a fluorescent material.

Additional features and advantages are described herein, and will be apparent from, the following Detailed Description and figures.

DETAILED DESCRIPTION

Figure 2:
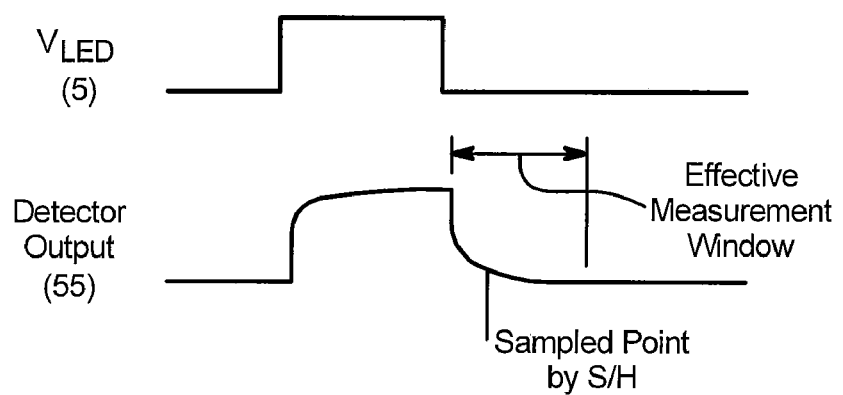
FIG. 2 shows a timing response for a classical time-resolved fluorescence measurement system.

The present disclosure provides methods and materials for detecting light (e.g., fluorescence) released from a labeling material. Such methods and devices may be employed in methods used to conduct an assay (e.g., a lateral flow assay). The methods and materials of the present disclosure offer advantages over the classical time resolve fluorescence detection system which requires that the detection of florescence material be done from the time between when the excitation source has been extinguished, to the time before the florescence signal decays to below the noise floor, as shown in FIG. 2. This timing restriction requires the excitation and detection electronics to be responsive within the decay time window of the florescent labels. Given that the decay times for florescent labels range from 100's of nS to below 1 nS, very fast electronic circuits are required to detect florescent labels in the 1 nS range. This problem is further complicated by an inverse relationship between sensitivity of the PIN photo-diode and the switching speed. For the PIN and TIA to switch quickly, a small PIN with low capacitance is needed. However, a smaller PIN will detect less light, and thus reduces sensitivity. Another issue is that for sensitive measurements, a high gain setting in the amplifier chain may be required. However, when the light source is turned on, the amplifier chain will saturate, and may require a finite time to recover after the light source is turned off. This recovery delay time could easily exceed the decay time window, which then would void the measurement. One method to avoid this saturation and recovery time of the amplifier chain is to dynamically boost the gain right after the light source is turned off. Again, a variable gain block with fast gain switching is required. This is difficult to implement, especially for label with short decay times (e.g., equal to or less than 1 nS). The present disclosure solves these problems by providing an architecture for a detection system that detects accumulated phase shifts in the form of a ring-oscillator frequency.

Figure 1:
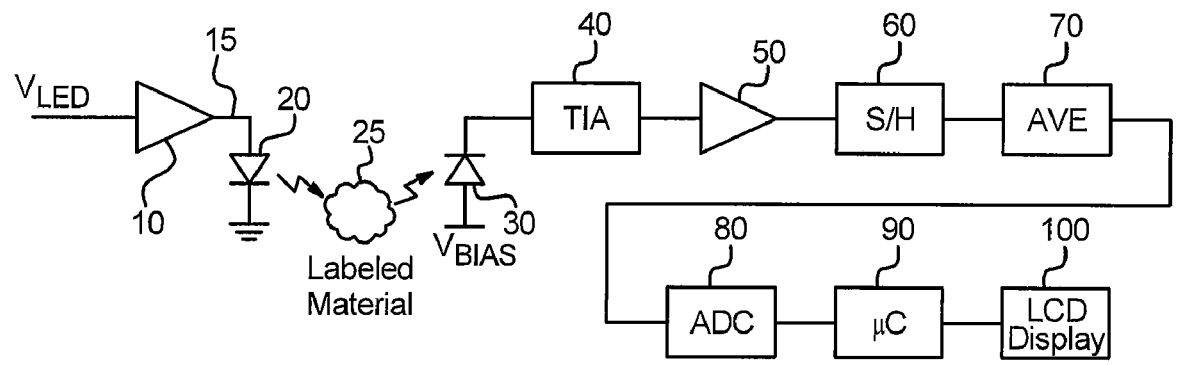
FIG. 1 depicts a classical time-resolved fluorescence measurement system.

The overall operating principle of the classical system depicted in FIG. 1 is different, in that in the classical system, a voltage is detected soon after the excitation is turned off. In the present disclosure, the accumulated phase shifts are detected, in the form of the ring-oscillator frequency. The new system's advantages over the classical system are: an integration yields a natural signal gain, whereby a small phase shift results in a detectable frequency change, it does not require fast gain adjustment to avoid saturation, it allows the use of larger PINs to be used for detection, it eliminates the need for a sample/hold circuit and it removes the need for an averaging filter. The natural averaging function arising from the integration of phase to frequency yields noise reduction leading to sensitive detection.

The systems, including devices of the present disclosure provide for detection of a light released by a labeling material, the device comprising: a start-up circuit; a pulse generator block that drives an LED driver, wherein the start-up circuit drives the pulse generator block; a photodetector that detects the light released by a labeling material and provides a first signal; a variable reference that provides a second signal; a slicer for comparing the first signal to the second signal, wherein the slicer generates an output signal with a delay that triggers the pulse generator block to drive the LED driver after the start-up circuit is disabled; a frequency reference; and a frequency counter for comparing the frequency of the output pulses from the slicer to the frequency reference thereby producing a output signal. The signal provided by the start-up circuit may be a brief signal of sufficient intensity to drive the pulse generator block before being disabled. Notably, the output signal from the slicer may continue to drive the pulse generator block and thus drive the LED driver until such time where the intensity of the output signal falls below a threshold required to drive the pulse generator block.

Such devices of the present disclosure may be employed in methods for detecting a light released by a labeling material, said method comprising: providing power to a pulse generator block; pulsing the labeling material with a light source, wherein the labeling material releases a light; detecting the light given off from the labeling material to produce a first signal; comparing the first signal produced by the labeling material to a second signal generated by a variable reference with a slicer to produce an output signal, wherein the output signal has a frequency and powers the pulse generator; comparing frequency from the output of the slicer to the frequency reference; and obtaining a measurement from the frequency converter.

The devices of the present disclosure may also be employed in methods for conducting an assay, the methods comprising: applying a test sample with at least one analyte to the assay; binding a labeling material to the analyte; providing power to a pulse generator block; pulsing the labeling material with a light source, wherein the labeling material releases a light; detecting the light given off from the labeling material to produce a first signal; comparing the first signal produced by the labeling material to a second signal generated by a variable reference with a slicer to produce an output signal, wherein the output signal has a frequency and powers the pulse generator; comparing frequency from the output of the slicer to the frequency reference; and obtaining a measurement from the frequency converter.

The present disclosure provides an architecture for use in detectors employed in immunoassay detection. Such detectors may be used to detect light released from a labeling material by detecting accumulated phase shifts in the form of a ring-oscillator frequency.

A device of the present disclosure may comprise a light source for excitation of a fluorescent labeling material. The device may comprise a start-up circuit including, for example, a pulsed current source, which drops out of the ring oscillator after application of a light source (e.g., a laser and/or a LED) to a labeling material. Light released from the labeling material may be detected by a photodetector such as a PIN photo diode. Optionally, the device may further comprises a transimpedance amplifier for amplifying the signal produced by the photodetector. The signal detected by the photodetector and a signal from a variable reference may be fed to a slicer. The variable reference may feed a signal to the slicer that is above a background noise. Background noise may include background light, dark current of the PIN diode, noise of the electronics used to drive the light source, and the noise of the electronic circuitry of the detector and amplifiers or combinations thereof. The output signal from the slicer is a pulse train whose frequency is directly related to the amount of labeling material detected. The frequency of the output form the slicer may be compared to a reference frequency (e.g., derived from a crystal source) by a frequency counter and differences in frequency between the output of the slicer and the reference frequency may be detected. Optionally, the device may further comprise a delay block to set a nominal period and/or an output for displaying the output signal on an output device including, for example, an LCD display.

Figure 3:
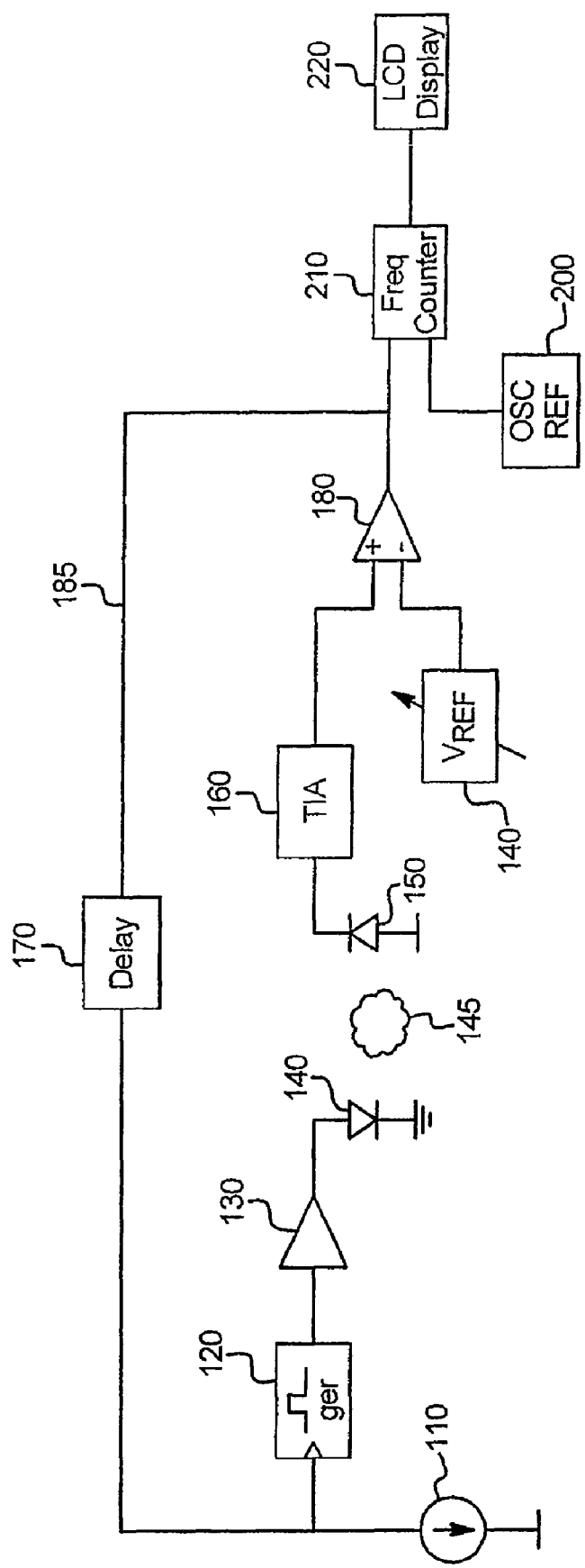
FIG. 3 shows a system architecture of the present disclosure.

An embodiment of the detection system architecture of the present disclosure is shown in FIG. 3. The pulse generator block 120 drives the LED driver 130, which is triggered by the output of the detector by slicer 180, with a delay 170. The overall structure of the system is a ring-oscillator. A delay block 170 may be inserted in the ring structure to set the overall nominal period. The delay block could include slight variability to compensate for the delay variations environmental changes such as temperature or supply voltages of the electrical and optical components of the ring oscillator loop, such that the overall delay around the loop is nominally constant. Additionally, a start-up circuit 110 including, for example, any type of high-impedance switching, such as a pulsed current source, is added to drive the pulse generator 120. Once the ring oscillator is running, the start-up circuit drops out of the ring oscillator loop. The detected light current from the PIN photo diode 150 may be amplified to a voltage signal by a transimpedance amplifier (TIA) 160. The output 165 of the TIA 160 may be compared with the output 195 of a variable reference 190, by the slicer 180. The resulting output 185 is a pulse train, whose frequency is directly related to the presence of the labeling material present.

The slight shift in phase caused by the florescent decay extends the ring oscillation period, which decreases the overall oscillation frequency. Furthermore, since frequency is an integral of phase, there is a natural integration, or averaging, function built-in to the system. The integration also results in an overall signal gain, whereby a very small shift in phase will manifest into a substantial shift in frequency. The frequency of the output signal 185 may be compared to a reference frequency signal 205 of high accuracy (e.g., derived from a crystal source 200) over a long gating period relative to the period (e.g., 1 second) by a frequency counter 210, and very minute changes in the frequency could be detected. As before, the output may be displayed with a LCD display 220.

The present disclosure may also be used to map a decay curve for a fluorescent label. By adjusting the threshold voltage block 190, and monitoring the output frequency, one could map out the entire decay curve of the florescent label. Such a map may be useful when there is more than one label present, and the decay curve signature is one way to distinguish one label from the other.

The methods of the present disclosure are preferably used with an immunoassay device. One or more analytes bound to an antibody on the surface of the immunoassay device may be detected and subsequently quantitated.

Exemplary assays contemplated for use with the methods of the present disclosure include lateral flow assay test strips. Lateral flow assay test strips may comprise a membrane system that forms a single fluid flow pathway along the test strip. The membrane system may include one or more components that act as a solid support for immunoreactions. For example, porous, bibulous or absorbent materials may be placed on a strip such that they partially overlap, or a single material can be used, in order to conduct liquid along the strip. The membrane materials may be supported on a backing, such as a plastic backing. In a preferred embodiment, the test strip includes a glass fiber pad, a nitrocellulose strip and an absorbent cellulose paper strip supported on a plastic backing.

Antibodies that react with the target analyte and/or a detectable label system are immobilized on the solid support. The antibodies may be bound to the test strip by adsorption, ionic binding, van der Waals adsorption, electrostatic binding, or by covalent binding, by using a coupling agent, such as glutaraldehyde. For example, the antibodies may be applied to the conjugate pad and nitrocellulose strip using standard dispensing methods, such as a syringe pump, air brush, ceramic piston pump or drop-on-demand dispenser. In a preferred embodiment, a volumetric ceramic piston pump dispenser may be used to stripe antibodies that bind the analyte of interest, including a labeled antibody conjugate, onto a glass fiber conjugate pad and a nitrocellulose strip. The test strip may or may not be otherwise treated, for example, with sugar to facilitate mobility along the test strip or with water-soluble non-immune animal proteins, such as albumins, including bovine (BSA), other animal proteins, water-soluble polyamino acids, or casein to block non-specific binding sites.

Any antibody, including polyclonal or monoclonal antibodies, or any fragment thereof, such as the Fab fragment, that binds the analyte of interest, is contemplated for use herein.

An antibody conjugate containing a detectable label may be used to bind the analyte of interest. The detectable label used in the antibody conjugate may be any physical or chemical label capable of being detected on a solid support using a reader, preferably a fluorescent reader, and capable of being used to distinguish the reagents to be detected from, other compounds and materials in the assay.

Suitable antibody labels are well known to those of skill in the art and include, but are not limited to, enzyme-substrate combinations that produce color upon reaction, colored particles, such as latex particles, colloidal metal or metal or carbon sol labels, fluorescent labels, and liposome or polymer sacs, which are detected due to aggregation of the label. In an embodiment, colloidal gold is used in the labeled antibody conjugate. The label may be derivatized for linking antibodies, such as by attaching functional groups, such as carboxyl groups to the surface of a particle to permit covalent attachment of antibodies. Antibodies may be conjugated to the label using well known coupling methods.

The assay test strip may be any conventional lateral flow assay test strip such as disclosed in EP 291194 or U.S. Pat. No. 6,352,862. The test strip may comprise a porous carrier containing a particulate labelled specific binding reagent and an unlabelled specific binding reagent. The light sources and corresponding photodetectors are preferably so aligned such that during use, light from the light source or sources falls upon the respective zones on the porous carrier and is reflected or transmitted to the respective photodetectors. The photodetectors generate a current roughly proportional to the amount of light falling upon it which is then fed through a resistor to generate a voltage. The amount of light reaching the photodetector depends upon the amount of coloured particulate label present and therefore the amount of analyte. Thus the amount of analyte present in the sample may be determined. This method of optically determining the analyte concentration is described more fully in EP 653625.

A sample may include, for example, anything which may contain an analyte of interest. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cells.

A fluid sample (e.g., biological fluid) may refer to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte.

Exemplary lateral flow devices include those described in U.S. Pat. Nos. 4,818,677, 4,943,522, 5,096,837 (RE 35,306), 5,096,837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5,939,331, 6,306,642.

A sample may include, for example, anything which may contain an analyte. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). A liquid sample may refer to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay. Typically, the sample is an aqueous solution or biological fluid as described in more detail below.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte.

An analyte can be any substance for which there exists a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunologically detected. That is, the analyte, or portion thereof, will be antigenic or haptenic having at least one determinant site, or will be a member of a naturally occurring binding pair.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof (see, e.g., U.S. Pat. Nos. 4,366,241; 4,299,916; 4,275,149; and 4,806,311).

In an embodiment, a sample receiving zone on the surface of a lateral flow assay test strip accepts a fluid sample that may contain one or more analytes of interest. In an embodiment, the sample receiving zone is dipped into a fluid sample. A label zone is located downstream of the sample receiving zone, and contains one or more mobile label reagents that recognize, or are capable of binding the analytes of interest. Further, a test region may be disposed downstream from the label zone, and contains test and control zones. The test zone(s) generally contain means which permit the restraint of a particular analyte of interest in each test zone. Frequently, the means included in the test zone(s) comprise an immobilized capture reagent that binds to the analyte of interest. Generally the immobilized capture reagent specifically binds to the analyte of interest. Thus, as the fluid sample flows along the matrix, the analyte of interest will first bind with a mobilizable label reagent in the label zone, and then become restrained in the test zone.

In an embodiment, the sample receiving zone may be comprised of an absorbent application pad. Suitable materials for manufacturing absorbent application pads include, but are not limited to, hydrophilic polyethylene materials or pads, acrylic fiber, glass fiber, filter paper or pads, desiccated paper, paper pulp, fabric, and the like. For example, the sample receiving zone may be comprised of a material such as a nonwoven spunlaced acrylic fiber.

The sample receiving zone may be comprised of any material from which the fluid sample can pass to the label zone. Further, the absorbent application pad can be constructed to act as a filter for cellular components, hormones, particulate, and other certain substances that may occur in the fluid sample. Application pad materials suitable for use by the present invention also include those application pad materials disclosed in U.S. Pat. No. 5,075,078.

In a further embodiment, the sample receiving zone may be comprised of an additional sample application member (e.g., a wick). Thus, in one aspect, the sample receiving zone can comprise a sample application pad as well as a sample application member. Often the sample application member is comprised of a material that readily absorbs any of a variety of fluid samples contemplated herein, and remains robust in physical form. Frequently, the sample application member is comprised of a material such as white bonded polyester fiber. Moreover, the sample application member, if present, is positioned in fluid-flow contact with a sample application pad.

In an embodiment, the label zone material may be treated with labeled solution that includes material-blocking and label-stabilizing agents. Blocking agents include, for example, bovine serum albumin (BSA), methylated BSA, casein, nonfat dry milk. Stabilizing agents are readily available and well known in the art, and may be used, for example, to stabilize labeled reagents.

The label zone may contain a labeled reagent, often comprising one or more labeled reagents. In many of the presently contemplated embodiments, multiple types of labeled reagents are incorporated in the label zone such that they may permeate together with a fluid sample contacted with the device. These multiple types of labeled reagent can be analyte specific or control reagents and may have different detectable characteristics (e.g., different colors) such that one labeled reagent can be differentiated from another labeled reagent if utilized in the same device. As the labeled reagents are frequently bound to a specific analyte of interest subsequent to fluid sample flow through the label zone, differential detection of labeled reagents having different specificities (including analyte specific and control labeled reagents) may be a desirable attribute. However, frequently, the ability to differentially detect the labeled reagents having different specificities based on the label component alone is not necessary due to the presence of test and control zones in the device, which allow for the accumulation of labeled reagent in designated zones.

The labeling zone may also include control-type reagents. These labeled control reagents often comprise detectable moieties that will not become restrained in the test zones and that are carried through to the test region and control zone(s) by fluid sample flow through the device. In a frequent embodiment, these detectable moieties are coupled to a member of a specific binding pair to form a control conjugate which can then be restrained in a separate control zone of the test region by a corresponding member of the specific binding pair to verify that the flow of liquid is as expected. The visible moieties used in the labeled control reagents may be the same or different color, or of the same or different type, as those used in the analyte of interest specific labeled reagents. If different colors are used, ease of observing the results may be enhanced.

The test region may include a control zone for verification that the sample flow is as expected. Each of the control zones comprise a spatially distinct region that often includes an immobilized member of a specific binding pair which reacts with a labeled control reagent. In an occasional embodiment, the procedural control zone contains an authentic sample of the analyte of interest, or a fragment thereof. In this embodiment, one type of labeled reagent can be utilized, wherein fluid sample transports the labeled reagent to the test and control zones; and the labeled reagent not bound to an analyte of interest will then bind to the authentic sample of the analyte of interest positioned in the control zone. In another embodiment, the control line contains antibody that is specific for, or otherwise provides for the immobilization of, the labeled reagent. In operation, a labeled reagent is restrained in each of the one or more control zones, even when any or all the analytes of interest are absent from the test sample.

Since the devices of the present invention may incorporate one or more control zones, the labeled control reagent and their corresponding control zones are preferably developed such that each control zone will become visible with a desired intensity for all control zones after fluid sample is contacted with the device, regardless of the presence or absence of one or more analytes of interest. In one embodiment, a single labeled control reagent will be captured by each of the control zones on the test strip. Frequently, such a labeled control reagent will be deposited onto or in the label zone in an amount exceeding the capacity of the total binding capacity of the combined control zones if multiple control zones are present. Accordingly, the amount of capture reagent specific for the control label can be deposited in an amount that allows for the generation of desired signal intensity in the one or more control zones, and allows each of the control zones to restrain a desired amount of labeled control-reagent. At the completion of an assay, each of the control zones preferably provide a desired and/or pre-designed signal (in intensity and form).

In an embodiment, each control zone will be specific for a unique control reagent. In this embodiment, the label zone may include multiple and different labeled control reagents, equaling the number of control zones in the assay, or a related variation. Wherein each of the labeled control reagents may become restrained in one or more pre-determined and specific control zone(s). These labeled control reagents can provide the same detectable signal (e.g., be of the same color) or provide distinguishable detectable signals (e.g., have different colored labels or other detection systems) upon accumulation in the control zone(s).

In an embodiment, the labeled control reagent comprises a detectable moiety coupled to a member of a specific binding pair. Typically, a labeled control reagent is chosen to be different from the reagent that is recognized by the means which are capable of restraining an analyte of interest in the test zone. Further, the labeled control reagent is generally not specific for the analyte. In a frequent embodiment, the labeled control reagent is capable of binding the corresponding member of a specific binding pair or control capture partner that is immobilized on or in the control zone. Thus the labeled control reagent is directly restrained in the control zone.

The use of a control zone is helpful in that appearance of a signal in the control zone indicates the time at which the test result can be read, even for a negative result. Thus, when the expected signal appears in the control line, the presence or absence of a signal in a test zone can be noted.

Test zones of the present description include means that permit the restraint of an analyte of interest. Frequently, test zones of the present description include a ligand that is capable of specifically binding to an analyte of interest. Alternatively, test zones of the present description include a ligand that is capable of specifically binding the labeled reagent bound to an analyte of interest. In practice, a labeled test reagent binds an analyte of interest present in a fluid sample after contact of the sample with a representative device and flow of the fluid sample into and through the label zone. Thereafter, the fluid sample containing the labeled analyte progresses to a test zone and becomes restrained in the test zone. The accumulation of labeled analyte in the test zone produces a detectable signal. Devices may incorporate one or more test zones, each of which is capable of restraining different analytes, if present, in a fluid sample. Thus, in representative embodiments two, three, four, five or more (labeled) analytes of interest can be restrained in a single or different test zones, and thereby detected, in a single device.

The present devices may optionally further comprise an absorbent zone that acts to absorb excess sample after the sample migrates through the test region. The absorbent zone, when present lies in fluid flow contact with the test region. This fluid flow contact can comprise an overlapping, abutting or interlaced type of contact. In an occasional embodiment, a control region (end of assay indicator) is provided in the absorbent zone to indicate when the assay is complete. In this embodiment, specialized reagents are utilized, such as pH sensitive reagents (such as bromocresol green), to indicate when the fluid sample has permeated past all of the test and control zones.

The test strip optionally may be contained within a housing for insertion into the reader. The housing may be made of plastic or other inert material that does not interfere with the assay procedure.

The lateral flow assay test strip may be suited for use with a reading device that comprises one or more of the following: a central processing unit (CPU) or microcontroller; one or more LED's or laser diodes; one or more photodiodes; a power source; and associated electrical circuitry. The power source may comprise a battery or any other suitable power source (e.g. a photovoltaic cell). The CPU will typically be programmed so as to determine whether the calculated rate and/or extent of progress of the liquid sample is within predetermined limits.

Conveniently the assay result reading device will comprise some manner of indicating the result of the assay to a user. This may take the form, for example, of an audible or visible signal. Desirably the device will comprise a visual display to display the assay result. This may simply take the form of one or more LED's or other light sources, such that illumination of a particular light source or combination of light sources conveys the necessary information to the user. Alternatively the device may be provided with an alphanumeric or other display, such as an LCD. In addition, or as an alternative, to displaying the assay result, the device may also display or indicate in some other way to the user whether the calculated rate and/or extent of progress of the liquid sample is within the predetermined acceptable limits, and thus whether or not the result of the particular assay should be disregarded. If the reading device determines that a particular assay result should be disregarded it may prompt the user to repeat the assay.

Any device which is compatible for use with an assay test strip, preferably a fluorescence reader, for determining the assay result is contemplated for use herein. Such test strip devices as are known to those of skill in the art (see, e.g., U.S. Pat. Nos. 5,658,801, 5,656,502, 5,591,645, 5,500,375, 5,252, 459, 5,132,097). Reflectance, Fluorescence and other readers, including densitometers and transmittance readers, are known to those of skill in the art (see, e.g., U.S. Pat. Nos. 5,598,007, 5,132,097, 5,094,955, 4,267,261, 5,118,183, 5,661,563, 4,647,544, 4,197,088, 4,666,309, 5,457,313, 3,905,767, 5,198,369, 4,400,353).

It should be understood by those skilled in the art that various modifications, combinations, sub-combinations and alterations may occur depending on design requirements and other factors insofar as they are within the scope of the appended claims or the equivalents thereof.

The invention claimed is:

1. A device comprising:
a pulse generator block that drives an LED driver;
a start-up circuit that drives the pulse generator block;
a photodetector that detects a light released by a labeling material and provides a first signal;
a variable reference that provides a second signal;
a slicer for comparing the first signal to the second signal, wherein the slicer generates an output signal with a delay that triggers the pulse generator block after the start-up circuit is disabled;
a frequency reference; and
a frequency counter for comparing the output from the slicer to the frequency reference thereby producing an output signal.

2. The device of claim 1, wherein the start-up circuit is a pulsed current source.

3. The device of claim 1, wherein the labeling material is a fluorescent material.

4. The device of claim 1, wherein the photodetector is a PIN photo diode.

5. The device of claim 1, wherein the reference frequency signal is from a crystal source.

6. The device of claim 1 further comprising a transimpedance amplifier for amplifying the signal produced by the photodetector.

7. The device of claim 1 further comprising a light source for excitation of a fluorescent label.

8. The device of claim 1, wherein the light source is a laser.

9. The device of claim 1, wherein the light source is a LED.

10. The device of claim 1 further comprising a delay block to set a nominal period.

11. The device of claim 1 further comprising displaying the output signal on an output device.

12. The method of claim 1, wherein the output device is an LCD display.

13. A method for detecting a light released by a labeling material, said method comprising:
   providing power to a start-up circuit that drives a pulse generator block;
   pulsing the labeling material with a light source, wherein the labeling material releases a light;
   detecting the light released from the labeling material to produce a first signal;
   comparing the first signal produced by the labeling material to a second signal generated by a variable reference with a slicer to produce an output signal, wherein the output signal has a frequency and triggers the pulse generator block after the start-up circuit is disabled;
   comparing frequency of the output pulses of the slicer to the frequency reference; and
   obtaining a measurement from the frequency converter.

14. The method of claim 13 further comprising converting the measurement from the frequency converter to a digital output that can be displayed on a user friendly interface.

15. The method of claim 13, wherein the user friendly interface is an LCD display.

16. The method of claim 13, wherein the light is amplified to a voltage signal by a transimpedance amplifier.

17. The method of claim 13, wherein the output is displayed with a LCD display.

18. The method of claim 13, wherein the light source is an LED.

19. The method of claim 13, wherein the light source is a laser.

20. The method of claim 13, wherein the variable reference is equal to a background level.

21. The method of claim 13, wherein the light is pulsed.

22. The method of claim 13, wherein the first and second signal are compared by a slicer.

23. The method of claim 13, wherein the light is detected by PIN photo diode.

24. The method of claim 13, wherein the frequency reference is from a crystal source.

25. The method of claim 13 further comprising a transimpedance amplifier for amplifying the signal produced by the photodetector.

26. The method of claim 13 further comprising a delay block to set a nominal period.

27. The method of claim 13, wherein the labeling material is a fluorescent material.

28. A method for conducting an assay, the method comprising:
   applying a test sample with at least one analyte to the assay;
   binding a labeling material to the analyte;
   providing power to a start-up circuit that drives a pulse generator block;
   pulsing the labeling material with a light source, wherein the labeling material releases a light;
   detecting the light released from the labeling material to produce a first signal;
   comparing the first signal produced by the labeling material to a second signal generated by a variable reference with a slicer to produce an output signal, wherein the output signal has a frequency and triggers the pulse generator block after the start-up circuit is disabled;
   comparing frequency from the output of the slicer to the frequency reference; and
   obtaining a measurement from the frequency converter.

29. The method of claim 28, wherein the assay is a lateral flow assay.

30. The method of claim 28 further comprising converting the measurement from the frequency converter to a digital output that can be displayed on a user friendly interface.

31. The method of claim 28, wherein the user friendly interface is an LCD display.

32. The method of claim 28, wherein the light is amplified to a voltage signal by a transimpedance amplifier.

33. The method of claim 28, wherein the output is displayed with a LCD display.

34. The method of claim 28, wherein the light source is an LED.

35. The method of claim 28, wherein the light source is a laser.

36. The method of claim 28, wherein the variable reference is above a background level.

37. The method of claim 28, wherein the light is pulsed.

38. The method of claim 28, wherein the first and second signal are compared by a slicer.

39. The method of claim 28, wherein the light is detected by PIN photo diode.

40. The method of claim 28, wherein the frequency reference is from a crystal source.

41. The method of claim 28 further comprising a transimpedance amplifier for amplifying the signal produced by the photodetector.

42. The method of claim 28 further comprising a resistor after the transimpedance amplifier.

43. The method of claim 28 further comprising a delay block to set a nominal period.

44. The method of claim 28, wherein the labeling material is a fluorescent material.

* * * * *